US008383401B2

(12) United States Patent
Shiku et al.

(10) Patent No.: US 8,383,401 B2
(45) Date of Patent: Feb. 26, 2013

(54) T-CELL RECEPTOR AND NUCLEIC ACID ENCODING THE RECEPTOR

(75) Inventors: Hiroshi Shiku, Tsu (JP); Atsunori Hiasa, Tsu (JP); Satoshi Okumura, Tsu (JP); Hiroaki Naota, Tsu (JP); Yoshihiro Miyahara, Houston, TX (US)

(73) Assignees: MIE University, Tsu-Shi (JP); Takara Bio Inc., Otsu-Shi (JP)

( * ) Notice: Subject to any disclaimer, the term of this patent is extended or adjusted under 35 U.S.C. 154(b) by 0 days.

(21) Appl. No.: 13/167,414

(22) Filed: Jun. 23, 2011

(65) Prior Publication Data

US 2011/0256114 A1 Oct. 20, 2011

Related U.S. Application Data

(62) Division of application No. 11/991,964, filed as application No. PCT/JP2006/317773 on Sep. 7, 2006, now Pat. No. 8,003,770.

(30) Foreign Application Priority Data

Sep. 13, 2005 (JP) ................................ 2005-266088

(51) Int. Cl.
*C07H 21/02* (2006.01)
*C12N 15/00* (2006.01)
*C12N 5/00* (2006.01)
*C12N 5/02* (2006.01)
*C12N 5/071* (2010.01)

(52) U.S. Cl. ... 435/325; 536/23.5; 536/23.1; 435/320.1; 435/372.3

(58) Field of Classification Search .................... 435/325
See application file for complete search history.

(56) References Cited

U.S. PATENT DOCUMENTS

| 6,064,292 | A | 5/2000 | Pongracz |
| 6,783,961 | B1 | 8/2004 | Edwards et al. |
| 2003/0082178 | A1 | 5/2003 | Gold et al. |
| 2005/0249743 | A1 | 11/2005 | Boon-Falleur et al. |
| 2006/0073126 | A1 | 4/2006 | Shiku et al. |
| 2006/0105336 | A1 | 5/2006 | Zang |

FOREIGN PATENT DOCUMENTS

| JP | 10-511542 A | 11/1998 |
| JP | 2004-506021 A | 2/2004 |
| JP | 2006-101735 A2 | 4/2006 |
| WO | 96/15238 A1 | 5/1996 |
| WO | 2004/015070 A2 | 2/2004 |
| WO | 2006/000830 A2 | 1/2006 |

OTHER PUBLICATIONS

Wittenberger, 2001, J Mol. Biol, 307:799-813.*
Aarnoudse, C. A. et al., "TCR Reconsitution in Jurkat Reporter Cells Facilitates the Identification of Novel Tumor Antigens by CDNA Expression Cloning," Int. J. Cancer, 2002, vol. 99, pp. 7-13.
Calogero, A. et al., "Retargeting of a T Cell Line by Anti Mage-3/HLA-A2 αβ TCR Gene Transfer," Anticancer Research, 2000, vol. 20, pp. 1793-1800.
Clay, T. M. et al., "Efficient Transfer of a Tumor Antigen-Reactive TCR to Human Peripheral Blood Lymphocytes Confers Anti-Tumor Reactivity," The Journal of Immunology, 1999, vol. 163, pp. 507-513.
Cole, D. J. et al., "Identification of MART-1-specific T-Cell Receptors: T Cells Utilizing Distinct T-Cell Receptor Variable and Joining Regions Recognize the Same Tumor Eptitope," Cancer Research, Oct. 15, 1994, vol. 54, pp. 5265-5268.
EPO Extended European Search Report, Appl. No. 06797633.2, Aug. 19, 2009, pp. 1-4.
Farina, C. et al., "Conserved TCR usage by HLA-Cw*1601-restricted T cell clones recognizing melanoma antigens," International Immunology, 1996, vol. 8, No. 9, pp. 1463-1466.
Gattinoni et al., "Adoptive immunotherapy for cancer: building on success," Nature Reviews Immunology, May 2006, vol. 6, No. 5, pp. 383-393, XP-002540348.
Genbank Acc. No. CD696833, US National Library of Medicine, Bethesda, MD, published Jun. 25, 2003, accessed by the PTO Oct. 14, 2010.
Genbank Acc. No. DQ36937, US National Library of Medicine, Bethesda, MD, published Jun. 2, 2005, accessed by the PTO Oct. 14, 2010.
Heemskerk, M.H.M. et al., "Redirection of antileukemic reactivity of peripheral T lymphocytes using gene transfer of minor histocompatibility antigen HA-2-specific T-cell receptor complexes expressing a conserved alpha joining region," Blood, Nov. 15, 2003, vol. 102, No. 10, pp. 3530-3540.
Hiasa et al., "Long-term phenotypic, functional and genetic stability of cancer-specific T-cell receptor (TCR) αβ genes transduced to CD8+ T cells," Gene Therapy, May 2008, vol. 15, No. 9, pp. 695-699, XP-002540350, published online Feb. 21, 2009.
Hiasa et al., "Rapid αβ TCR-mediated responses in γδ T cells transduced with cancer-specific TCR genes," Gene Therapy, May 2009, vol. 16, No. 5, pp. 620-628, XP-002540349, published online Feb. 26, 2008.
JPO International Search Report, Appl. No. PCT/JP2006/317773, Nov. 28, 2006, pp. 1-4.
Kennell, D.E., "Principles and Practices of Nucleic Acid Hybridization," Progr. Nucl. Acid Res. Mol. Biol., 1971, vol. 11, pp. 259-301.
Lake et al., "Construction and binding analysis of recombinant single-chain TCR derived from tumor-infiltrating lymphocyte clone directed against MAGE-1," International Immunology, The Japanese Society of Immunology, vol. 11, No. 5, pp. 745-751, 1999, XP002943355.
Miyahara, Y. et al, "Determination of Cellularly Processed HLA-A2402-Restricted Novel CTL Epititopes Derived from Two Cancer Germ Line Genes, MAGE-A4 and SAGE," Clinical Cancer Research, Aug. 2005, vol. 11, No. 15, pp. 5581-5589.

(Continued)

*Primary Examiner* — Valarie Bertoglio
(74) *Attorney, Agent, or Firm* — Birch, Stewart, Kolasch & Birch, LLP

(57) ABSTRACT

A polypeptide comprising a polypeptide consisting of an amino acid sequence shown in SEQ ID NO: 5 of Sequence Listing or a polypeptide consisting of an amino acid sequence having deletion, addition, insertion or substitution of one to several amino acid residues in the sequence, the polypeptide being capable of constituting an HLA-A24-restricted, MAGE-A4$_{143-151}$-specific T cell receptor together with a polypeptide consisting of an amino acid sequence shown in SEQ ID NO: 2 of Sequence Listing.

20 Claims, 2 Drawing Sheets
(2 of 2 Drawing Sheet(s) Filed in Color)

OTHER PUBLICATIONS

Okayama, H. et al, "High-Efficiency Cloning of Full-Length cDNA," Molecular and Cellular Biology, Feb. 1982, vol. 2, No. 2, pp. 161-170.

Ottaviani, S. et al, "A new MAGE-4 antigenic peptide recognized by cytolytic T lymphocytes on HLA-A24 carcinoma cells," Cancer Immunology Immunotherapy, Published online Sep. 3, 2005, vol. 55, No. 7, pp. 867-872.

PCT Written Opinion of International Searching Authority, Appl. No. PCT/JP2006/317773, Nov. 28, 2006, pp. 1-7.

Schaft, N. et al., "Peptide Fine Specificity of Anti-Glycoprotein 100 CTL is Preserved Following Transfer of Engineered TCRαβ Genes Into Primary Human T Lymphocytes1," The Journal of Immunology, 2003, vol. 170, pp. 2186-2194.

Tsuji, T. et al., "Generation of tumor-specific, HLA class I-restricted human Th1 and Tc1 cells by cell engineering with tumor peptide-specific T-cell receptor genes," Blood, Jul. 15, 2005, vol. 106, No. 2, pp. 470-476.

USPTO Notice of Allowance, U.S. Appl. No. 11/991,964, Mar. 24, 2011, pp. 1-7.

USPTO Office Action, U.S. Appl. No. 11/991,964, Oct. 20, 2010, pp. 1-22.

Willemsen et al., "Genetic Engineering of T Cell Specificity for Immunotherapy of Cancer," Human Immunology, Jan. 1, 2003, vol. 64, No. 1, pp. 56-68, XP-002336794.

Willemsen et al., "Redirecting human CD4+ T lymphocytes to the MHC class I-restricted melanoma antigen MAGE-A1 by TCR αβ gene transfer requires CD8α," Gene Therapy, Jan. 1, 2005, vol. 12, No. 2, pp. 140-146, XP003022404, published online Oct. 21, 2004.

Yoshikai, Y. et al., "Sequences and Repertoire of Human T Cell Receptor α Chain Variable Region Genes in Mature T Lymphycytes," J. Exp. Med., 1986, vol. 164, No. 1, pp. 90-103.

Zhao, Y. et al., "Primary Human Lymphocytes Transduced with NY-ESO-1 Antigen-Specific TCR Genese Recognize and Kill Diverse Human Tumor Cell Lines," The Journal of Immunology, 2005, vol. 174, pp. 4415-4423.

\* cited by examiner

SEQUENCE LISTING

<160> NUMBER OF SEQ ID NOS: 15

<210> SEQ ID NO 1
<211> LENGTH: 272
<212> TYPE: PRT
<213> ORGANISM: Homo sapiens

<400> SEQUENCE: 1

Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Ser Phe Asn Leu Arg
                85                  90                  95

Lys Pro Ser Val Gln Trp Ser Asp Thr Ala Glu Tyr Phe Cys Ala Gly
            100                 105                 110

Arg Gly Gly Asn Lys Leu Thr Phe Gly Thr Gly Thr Gln Leu Lys
            115                 120                 125

Val Glu Leu Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 2
<211> LENGTH: 313
<212> TYPE: PRT
<213> ORGANISM: Homo sapiens

<400> SEQUENCE: 2

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

```
Asn Arg Leu Tyr Trp Tyr Arg Gln Thr Leu Gly Gln Gly Pro Glu Phe
 50                  55                  60
Leu Thr Tyr Phe Gln Asn Glu Ala Gln Leu Glu Lys Ser Arg Leu Leu
 65                  70                  75                  80
Ser Asp Arg Phe Ser Ala Glu Arg Pro Lys Gly Ser Phe Ser Thr Leu
                 85                  90                  95
Glu Ile Gln Arg Thr Glu Gln Gly Asp Ser Ala Met Tyr Leu Cys Ala
                100                 105                 110
Ser Ser Leu Ala Gln Gly Ala Gly Glu Thr Gln Tyr Phe Gly Pro Gly
            115                 120                 125
Thr Arg Leu Leu Val Leu Glu Asp Leu Lys Asn Val Phe Pro Pro Glu
130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Tyr Pro Asp His Val Glu
                165                 170                 175
Leu Ser Trp Trp Val Asn Gly Lys Glu Val His Ser Gly Val Ser Thr
                180                 185                 190
Asp Pro Gln Pro Leu Lys Glu Gln Pro Ala Leu Asn Asp Ser Arg Tyr
            195                 200                 205
Cys Leu Ser Ser Arg Leu Arg Val Ser Ala Thr Phe Trp Gln Asn Pro
210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Glu Ser Tyr
                260                 265                 270
Gln Gln Gly Val Leu Ser Ala Thr Ile Leu Tyr Glu Ile Leu Leu Gly
            275                 280                 285
Lys Ala Thr Leu Tyr Ala Val Leu Val Ser Ala Leu Val Leu Met Ala
290                 295                 300
Met Val Lys Arg Lys Asp Ser Arg Gly
305                 310

<210> SEQ ID NO 3
<211> LENGTH: 819
<212> TYPE: DNA
<213> ORGANISM: Homo sapiens

<400> SEQUENCE: 3
atgctcctgt tgctcatacc agtgctgggg atgattttg ccctgagaga tgccagagcc      60
cagtctgtga gccagcataa ccaccacgta attctctctg aagcagcctc actggagttg     120
ggatgcaact attcctatgg tggaactgtt aatctcttct ggtatgtcca gtaccctggt     180
caacaccttc agcttctcct caagtacttt tcaggggatc cactggttaa aggcatcaag     240
ggctttgagg ctgaatttat aaagagtaaa ttctcccttta atctgaggaa accctctgtg     300
cagtggagtg acacagctga gtacttctgt gccggagggg aggaggaaa caaactcacc      360
tttgggacag gcactcagct aaaagtggaa ctcaatatcc agaaccctga ccctgccgtg     420
taccagctga gagactctaa atccagtgac aagtctgtct gcctattcac cgattttgat    480
tctcaaacaa atgtgtcaca agtaaggat tctgatgtgt atatcacaga caaaactgtg     540
ctagacatga ggtctatgga cttcaagagc aacagtgctg tggcctggag caacaaatct     600
gactttgcat gtgcaaacgc cttcaacaac agcattattc cagaagacac cttcttcccc    660
```

-continued

```
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagctga                            819
```

<210> SEQ ID NO 4
<211> LENGTH: 942
<212> TYPE: DNA
<213> ORGANISM: Homo sapiens

<400> SEQUENCE: 4

```
atgggcacca gcctcctctg ctggatggcc ctgtgtctcc tgggggcaga tcacgcagat     60
actggagtct cccagaaccc cagacacaag atcacaaaga ggggacagaa tgtaactttc    120
aggtgtgatc caatttctga acacaaccgc ctttattggt accgacagac cctggggcag    180
ggcccagagt ttctgactta cttccagaat gaagctcaac tagaaaaatc aaggctgctc    240
agtgatcggt tctctgcaga gaggcctaag ggatctttct ccaccttgga gatccagcgc    300
acagagcagg gggactcggc catgtatctc tgtgccagca gcttagccca gggagcggga    360
gagacccagt acttcgggcc aggcacgcgg ctcctggtgc tcgaggacct gaaaaacgtg    420
ttcccacccg aggtcgctgt gtttgagcca tcagaagcag agatctccca cacccaaaag    480
gccacactgg tatgcctggc cacaggcttc taccccgacc acgtggagct gagctggtgg    540
gtgaatggga aggaggtgca cagtggggtc agcacagacc cgcagcccct caaggagcag    600
cccgccctca tgactccaga tactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt cacctccgag tcttaccagc aaggggtcct gtctgccacc    840
atcctctatg agatcttgct agggaaggcc accttgtatg ccgtgctggt cagtgccctc    900
gtgctgatgg ccatggtcaa gagaaaggat tccagaggct ag                       942
```

<210> SEQ ID NO 5
<211> LENGTH: 131
<212> TYPE: PRT
<213> ORGANISM: Homo sapiens

<400> SEQUENCE: 5

```
Met Leu Leu Leu Leu Ile Pro Val Leu Gly Met Ile Phe Ala Leu Arg
1               5                   10                  15

Asp Ala Arg Ala Gln Ser Val Ser Gln His Asn His His Val Ile Leu
            20                  25                  30

Ser Glu Ala Ala Ser Leu Glu Leu Gly Cys Asn Tyr Ser Tyr Gly Gly
        35                  40                  45

Thr Val Asn Leu Phe Trp Tyr Val Gln Tyr Pro Gly Gln His Leu Gln
    50                  55                  60

Leu Leu Leu Lys Tyr Phe Ser Gly Asp Pro Leu Val Lys Gly Ile Lys
65                  70                  75                  80

Gly Phe Glu Ala Glu Phe Ile Lys Ser Lys Phe Ser Phe Asn Leu Arg
                85                  90                  95

Lys Pro Ser Val Gln Trp Ser Asp Thr Ala Glu Tyr Phe Cys Ala Gly
            100                 105                 110

Arg Gly Gly Gly Asn Lys Leu Thr Phe Gly Thr Gly Thr Gln Leu Lys
        115                 120                 125

Val Glu Leu
```

<210> SEQ ID NO 6
<211> LENGTH: 393
<212> TYPE: DNA
<213> ORGANISM: Homo sapiens

<400> SEQUENCE: 6

```
atgctcctgt tgctcatacc agtgctgggg atgattttg ccctgagaga tgccagagcc    60
cagtctgtga gccagcataa ccaccacgta attctctctg aagcagcctc actggagttg   120
ggatgcaact attcctatgg tggaactgtt aatctcttct ggtatgtcca gtaccctggt   180
caacaccttc agcttctcct caagtacttt tcaggggatc cactggttaa aggcatcaag   240
ggctttgagg ctgaatttat aaagagtaaa ttctcccttta atctgaggaa accctctgtg   300
cagtggagtg acacagctga gtacttctgt gccgggaggg gaggaggaaa caaactcacc   360
tttgggacag gcactcagct aaaagtggaa ctc                                 393
```

<210> SEQ ID NO 7
<211> LENGTH: 134
<212> TYPE: PRT
<213> ORGANISM: Homo sapiens

<400> SEQUENCE: 7

```
Met Gly Thr Ser Leu Leu Cys Trp Met Ala Leu Cys Leu Leu Gly Ala
1               5                   10                  15
Asp His Ala Asp Thr Gly Val Ser Gln Asn Pro Arg His Lys Ile Thr
            20                  25                  30
Lys Arg Gly Gln Asn Val Thr Phe Arg Cys Asp Pro Ile Ser Glu His
        35                  40                  45
Asn Arg Leu Tyr Trp Tyr Arg Gln Thr Leu Gly Gln Gly Pro Glu Phe
    50                  55                  60
Leu Thr Tyr Phe Gln Asn Glu Ala Gln Leu Glu Lys Ser Arg Leu Leu
65                  70                  75                  80
Ser Asp Arg Phe Ser Ala Glu Arg Pro Lys Gly Ser Phe Ser Thr Leu
                85                  90                  95
Glu Ile Gln Arg Thr Glu Gln Gly Asp Ser Ala Met Tyr Leu Cys Ala
            100                 105                 110
Ser Ser Leu Ala Gln Gly Ala Gly Glu Thr Gln Tyr Phe Gly Pro Gly
        115                 120                 125
Thr Arg Leu Leu Val Leu
    130
```

<210> SEQ ID NO 8
<211> LENGTH: 402
<212> TYPE: DNA
<213> ORGANISM: Homo sapiens

<400> SEQUENCE: 8

```
atgggcacca gctcctctg ctggatggcc ctgtgtctcc tggggcaga tcacgcagat    60
actggagtct cccagaaccc cagacacaag atcacaaaga ggggacagaa tgtaactttc   120
aggtgtgatc caatttctga acacaaccgc ctttattggt accgacagac cctggggcag   180
ggcccagagt ttctgactta cttccagaat gaagctcaac tagaaaaatc aaggctgctc   240
agtgatcggt tctctgcaga gaggcctaag ggatctttct ccaccttgga gatccagcgc   300
acagagcagg gggactcggc catgtatctc tgtgccagca gcttagccca gggagcggga   360
gagacccagt acttcgggcc aggcacgcgg ctcctggtgc tc                       402
```

<210> SEQ ID NO 9
<211> LENGTH: 9
<212> TYPE: PRT
<213> ORGANISM: Homo sapiens

<400> SEQUENCE: 9

Asn Tyr Lys Arg Cys Phe Pro Val Ile
1               5

<210> SEQ ID NO 10
<211> LENGTH: 40
<212> TYPE: DNA
<213> ORGANISM: Artificial sequence
<220> FEATURE:
<223> OTHER INFORMATION: Oligo dT adaptor - synthetic DNA

<400> SEQUENCE: 10
ctgtgaatgc tgcgactacg attttttttt tttttttttt                              40

<210> SEQ ID NO 11
<211> LENGTH: 22
<212> TYPE: DNA
<213> ORGANISM: Artificial sequence
<220> FEATURE:
<223> OTHER INFORMATION: 5'-RACE primer - synthetic DNA

<400> SEQUENCE: 11
gtctaccagg cattcgcttc at                                                 22

<210> SEQ ID NO 12
<211> LENGTH: 24
<212> TYPE: DNA
<213> ORGANISM: Artificial sequence
<220> FEATURE:
<223> OTHER INFORMATION: Synthetic primer 3-TRalpha-C to amplify a DNA
      fragment encoding TCR alpha chain

<400> SEQUENCE: 12
tcagctggac cacagccgca gcgt                                               24

<210> SEQ ID NO 13
<211> LENGTH: 21
<212> TYPE: DNA
<213> ORGANISM: Artificial sequence
<220> FEATURE:
<223> OTHER INFORMATION: Synthetic primer 3-TRbeta-C1 to amplify a DNA
      fragment encoding TCR beta chain

<400> SEQUENCE: 13
tcagaaatcc tttctcttga c                                                  21

<210> SEQ ID NO 14
<211> LENGTH: 24
<212> TYPE: DNA
<213> ORGANISM: Artificial sequence
<220> FEATURE:
<223> OTHER INFORMATION: Synthetic primer 3-TRbeta-C2 to amplify a DNA
      fragment encoding TCR beta chain

<400> SEQUENCE: 14
ctagcctctg gaatcctttc tctt                                               24

<210> SEQ ID NO 15
<211> LENGTH: 9
<212> TYPE: PRT
<213> ORGANISM: Homo sapiens

```
<400> SEQUENCE: 15

Leu Tyr Ala Thr Val Ile His Asp Ile
1               5
```

T-CELL RECEPTOR AND NUCLEIC ACID ENCODING THE RECEPTOR

This application is a Division of application Ser. No. 11/991,964, filed on Dec. 10, 2008, now U.S. Pat. No. 8,003,770, issued on Aug. 23, 2011, which is the national stage application of PCT International Application No. PCT/JP2006/317773, filed Sep. 7, 2006. The present application also claims the benefit of priority of Japanese Patent Application No. 2005-266088, filed Sep. 13, 2005. The entire contents of all are hereby incorporated by reference.

TECHNICAL FIELD

The present invention relates to a polypeptide constituting an α-chain of an HLA-A2402-restricted T cell receptor (TCR) specific to MAGE-A4$_{143\text{-}151}$, a nucleic acid encoding the polypeptide, a polypeptide constituting a β-chain of the above-mentioned TCR, a nucleic acid encoding the polypeptide, a T cell receptor containing the above-mentioned polypeptide constituting the α-chain and the above-mentioned polypeptide constituting the β-chain, a recombinant nucleic acid containing the nucleic acid, a vector carrying the recombinant nucleic acid, a cell into which the above-mentioned nucleic acid or vector is transduced, and a carcinostatic agent containing as an active ingredient the above-mentioned vector or cell.

BACKGROUND ART

Cytotoxic T cells (CTLs) include those capable of recognizing a complex by a specific T cell receptor (hereinafter simply referred to as "TCR"), the complex that is a conjugate of a major histocompatibility gene complex (hereinafter simply referred to as "MHC")-encoding major histocompatibility antigen molecule (MHC molecule; in a case of human, it is called "human leukocyte antigen," hereinafter simply referred to as "HLA") and an antigen peptide, and killing a cell in which the complex is presented on a cell surface. Therefore, in order to establish the cytotoxic reaction, it is necessary that 1) a CTL having a TCR specific to HLA Class I type of a target cell exists, and 2) an antigen peptide so that a complex formed by binding to the HLA molecule is capable of being recognized by the TCR exists.

The antigen peptide as described above is generated by, for example, processing an antigen or the like synthesized in a cell of a mammalian cell in a cytoplasm, thereby degrading into small peptides. The small peptides are further associated with an HLA molecule to be presented on the cell surface. In other words, in the proteasome complex consisting of numerous subunits, a protein is degraded into peptides consisting of 8 to 15 amino acids, some of which are transported from the cytoplasm to the endoplasmic reticulum by a TAP transporter. Once these peptides can be bound to a heterodimer of Class I/β2 microglobulin, they are stabilized in the form of a trimolecular complex, and transported to the cell surface through the Golgi apparatus. A tumor cell expressing a tumor-associated antigen or tumor-specific antigenic protein is supposedly capable of presenting an HLA-restricted antigenic peptide recognized by a T cell.

It has been known that the HLA Class I molecules are mainly HLA-A, -B, and -C, that the antigen peptides which are presented by binding to these molecules consist of 8 to 10 amino acids, and further that there are given different structural features for each of the HLA molecules. For example, as a peptide binding to an HLA-A2.1 molecule which is most frequently found worldwide, a peptide consisting of 9 to 10 amino acids, the peptide having Leu at a second position from an N-terminal, and Leu or Val at a C terminal has been most well known. In addition, as a peptide binding to an HLA-A24 molecule which is found more richly in the Asians such as the Japanese, a peptide consisting of 9 to 10 amino acids, the peptide having any one of Tyr, Phe, Met, and Trp at a second position from an N-terminal, and any one of Leu, Ile, Trp, and Phe at a C-terminal has been most well known.

Tumor antigens for which antigen peptides have so far been identified are MAGE-A1, MAGE-A3, and MAGE-A4 against HLA-A1; MAGE-A3, MART1, tyrosinase, gp100, HER2/neu, CEA and the like against HLA-A2.1; MAGE-A3 against HLA-Cw1; MAGE-A3 against HLA-B44; MAGE-A4 against HLA-B37; and MAGE-A1, MAGE-A2, MAGE-A3, MAGE-A4, NY-ESO-1, CEA, HER2/neu, tyrosinase, β-catenin, and the like against HLA-A24. In many of these tumor antigens, first, a cell line is established for a Class I-restricted CTL recognizing a tumor cell, a tumor antigen recognized by the CTL is identified, a minimum unit in tumor antigen proteins is subsequently found by a genetic engineering method, and peptides in the minimum unit are further found on the basis of the information regarding the binding motif to the HLA Class I molecules. In addition, first, peptides binding to the HLA Class I molecules are found in the tumor antigen proteins on the basis of the motif structure commonly shared between the above-mentioned peptides binding to the HLA Class I molecules, those peptides from which CTLs are inducible are subsequently selected utilizing an antigen presenting cell, and finally antigen peptides are then determined depending upon whether or not a CTL having toxicity against a tumor cell can be induced.

On the other hand, the HLA Class I molecules are classified into some subtypes, and the kinds of owned subtypes greatly differ among races. Worldwide, HLA-A2 is most often found, and 45% of the Caucasians are HLA-A2-positive. Moreover, the identification of this HLA-A2-restricted antigen peptide is most advanced. In the Japanese, HLA-A2-positive is found in 40%, and when their subtypes are studied, HLA-A*0201-positive, which is the same as the Caucasians, is 20%, and much of the remaining are A*0206-positive. The binding peptides to these subtypes are different, so that HLA-A2 that is mainly studied is HLA-A*0201. On the other hand, in the Japanese, HLA-A24-positive is found in 60% or more, and an HLA-A24-positive percentage is higher in the Asians than other races. Therefore, the finding of an HLA-A24-restricted antigen peptide plays an important role in providing a CTL that is useful in the treatment of tumor by inducing a CTL acting specifically to a tumor cell in the Asians, especially the Japanese.

Since antigen peptides differ on the basis of the difference in the HLA even with the same antigen, the induction of a CTL utilizing antigen peptides is complicated. Although various contrivances have been made in order to solve this disadvantage, a satisfactory fruit has not yet been obtained. One contrivance is a method including the steps of transducing an antigenic gene into an antigen presenting cell derived from a patient him/herself (self), and inducing a T cell utilizing the transformed gene. As the antigen presenting cell, B cell, macrophage, and dendritic cell have been studied, and a clinical test has been carried out using as an adjuvant or the like for a vaccine centering about dendritic cell which is known as a professional antigen presenting cell. However, there is a disadvantage that much labor is required in furnishing these antigen presenting cells in an amount necessary for immune induction. B cell can be mass-produced by immortalization by EB virus; however, there is a disadvantage in safety from the viewpoint of use of a virus.

As tumor antigen-specific TCR genes, for example, genes such as HLA-A2-restricted, MART1-specific TCR [Non-Patent Publication 1], MAGE-A3-specific TCR [Non-Patent Publication 2], CAMEL (CTL-recognized antigen on melanoma)-specific TCR [Non-Patent Publication 3], gp100-specific TCR [Non-Patent Publication 4], NY-ESO-1-specific TCR [Non-Patent Publication 5], HLA-24-restricted WT1 (Wilms tumor 1)-specific TCR [Non-Patent Publication 6], HLA-Cw16-restricted MAGE-A1-specific TCR [Non-Patent Publication 7] have been cloned.

It can be expected to give a specific cytotoxic activity to an intended antigen by transducing TCR gene into a given CTL. Based on the above, gene therapies with TCR gene targeted to MART1 [Non-Patent Publication 8], gp100 [Non-Patent Publication 4] and mHAG HA-2 antigen [Non-Patent Publication 9] have been tried.

MAGE-A4 is an antigen belonging to a MAGE subfamily of a cancer-testis antigen family, which is expressed in various cancers and has a high antigenicity (positive in 60% of esophageal cancer, 50% of head and neck cancers, 24% of non-small cell pulmonary cancer, 33% of stomach cancer, and 21% of Hodgkin disease), so that the antigen is expected to serve as a target antigen in cancer vaccine therapy. An HLA-A24-restricted MAGE-A4$_{143-151}$ peptide-specific CTL clone has been obtained [Non-Patent Publication 10].

Non-Patent Publication 1: *Cancer Res.*, 54, 5265-5268 (1994)
Non-Patent Publication 2: *Anticancer Res.*, 20, 1793-1799 (2000)
Non-Patent Publication 3: *Int. J. Cancer*, 99, 7-13 (2002)
Non-Patent Publication 4: *J. Immunol.* 170, 2186-2194 (2003)
Non-Patent Publication 5: *J. Immunol.*, 174, 4415-4423 (2005)
Non-Patent Publication 6: *Blood*, 106, 470-476 (2005)
Non-Patent Publication 7: *Int. Immunol.*, 8, 1463-1466 (1996)
Non-Patent Publication 8: *J. Immunol.*, 163, 507-513 (1999)
Non-Patent Publication 9: *Blood*, 103, 3530-3540 (2003)
Non-Patent Publication 10: *Clin. Cancer Res.*, 11, 5581-5589 (2005)

DISCLOSURE OF INVENTION

Problems to be Solved by the Invention

As an HLA-A24-restricted TCR gene against a tumor-associated antigen, those genes against WT1 have been known, but the analyses therefor have still been delayed as compared to those of HLA-A2.1, thereby making it impossible to provide TCR genes that are useful in the treatment of tumor for the Asians, especially the Japanese. Therefore, a finding of new, HLA-A24-restricted TCR genes against various tumor antigens has been desired.

One that plays the role of cytotoxic activity via the TCR in the living body is a CTL having antigen-specific TCRs, and there are some disadvantages in the handling of these cells, for example, collecting and expanding the cells, in order to use them for the treatment of a disease such as cancer by proliferating the CTLs ex vivo. Therefore, it has been earnestly desired to provide TCR gene specific to a tumor antigen or the like, in order to massively and easily prepare CTLs having a desired antigen-specificity.

Means to Solve the Problems

As a result of intensive studies on the CTL against the tumor antigen, the present inventors have succeeded in cloning cDNAs encoding α-chain and β-chain of the TCR from the HLA-A24-restricted CTL against a tumor antigen MAGE-A4. Further, a cell, such as a CTL, expressing an HLA-A24 molecule shows cytotoxicity specific to a peptide derived from HLA-A24-restricted MAGE-A4 by transducing RNA prepared from these cDNAs into these cells, and the present invention has been accomplished thereby.

A first embodiment of the present invention relates to a polypeptide constituting an HLA-A24-restricted, MAGE-A4$_{143-151}$-specific T cell receptor, and a polypeptide comprising a variable region polypeptide of the above-mentioned receptor.

A second embodiment of the present invention relates to an HLA-A24-restricted, MAGE-A4$_{143-151}$-specific TCR, characterized in that the TCR contains the polypeptide as defined in the first embodiment of the present invention.

A third embodiment of the present invention relates to a nucleic acid encoding an HLA-A24-restricted, MAGE-A4$_{143-151}$-specific TCR, and nucleic acid encoding a polypeptide comprising a variable region polypeptide of the above-mentioned receptor.

A fourth embodiment of the present invention relates to a recombinant nucleic acid containing the nucleic acid as defined in the third embodiment of the present invention.

A fifth embodiment of the present invention relates to a vector carrying the recombinant nucleic acid as defined in the fourth embodiment of the present invention, wherein the recombinant nucleic acid is inserted into the vector.

A sixth embodiment of the present invention relates to a cell which expresses an HLA-A24-restricted, MAGE-A4$_{143-151}$-specific TCR, characterized in that the nucleic acid as defined in the third embodiment of the present invention is transduced into the cell, or the cell is transformed with the vector as defined in the fifth embodiment.

A seventh embodiment of the present invention relates to a carcinostatic agent, characterized in that the carcinostatic agent contains as an active ingredient the cell as defined in the sixth embodiment of the present invention or the vector as defined in the fifth embodiment.

An eighth embodiment of the present invention relates to a method of treating cancer, including the step of administering the carcinostatic agent as defined in the seventh embodiment of the present invention.

Effects of the Invention

According to the present invention, a nucleic acid encoding an α-chain and β-chain of an HLA-A24-restricted, MAGE-A4$_{143-151}$-specific TCR is provided. In addition, a method for damaging a tumor cell using an HLA-A24-non-restricted, or MAGE-A4$_{143-151}$-non-specified T cell as an effector cell is provided. The above-mentioned effector cell is useful, for example, in the treatment of cancer.

BRIEF DESCRIPTION OF THE DRAWINGS

The patent or application file contains at least one drawing executed in color. Copies of this patent or patent application publication with color drawing(s) will be provided by the office upon request and payment of the necessary fee.

BEST MODE FOR CARRYING OUT THE INVENTION

Figure 1:
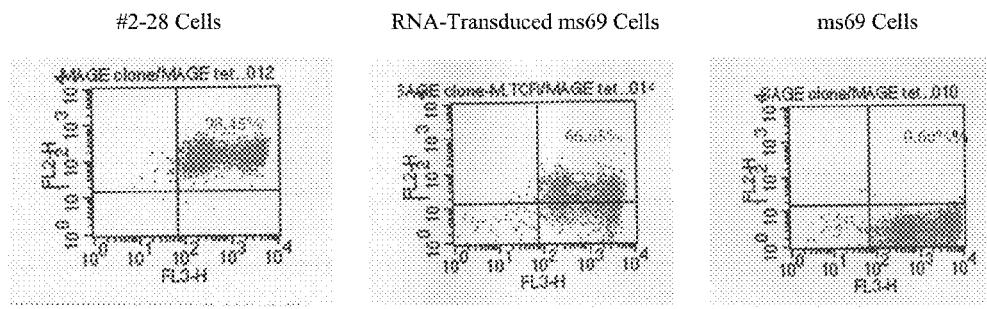
[FIG. 1] Graphs showing the results of tetramer assay of #2-28 cells, RNA-transduced ms69 cells, and ms69 cells.

A first embodiment of the present invention relates to a polypeptide constituting an HLA-A24-restricted, MAGE-A4$_{143-151}$-specific T cell receptor, the polypeptide comprising a variable region polypeptide of the above-mentioned receptor. There are two kinds of the above-mentioned polypeptides, TCR α-chain and TCR β-chain polypeptides, and both chains are combined to constitute an HLA-A24-restricted, MAGE-A4$_{143-151}$-specific TCR.

The above-mentioned α-chain polypeptide is capable of forming an HLA-A24-restricted, MAGE-A4$_{143-151}$-specific TCR together with that of a β-chain, and the phrase "α-chain polypeptide" means a polypeptide comprising an α-chain variable region polypeptide selected from a polypeptide of the amino acid sequence shown in SEQ ID NO: 5 of Sequence Listing, and a polypeptide having deletion, addition, insertion or substitution of one to several amino acid residues in the amino acid sequence shown in SEQ ID NO: 5 of Sequence Listing. The polypeptide derived from an α-chain of the TCR in the present invention contains as an essential constituent the above-mentioned amino acid sequence of an α-chain variable region, or a sequence similar thereto. A polypeptide consisting of the amino acid sequence of the entire α-chain (SEQ ID NO: 1) or a sequence similar thereto, i.e. an amino acid sequence having deletion, addition, insertion or substitution of one to several amino acid residues, the sequence containing a constant region, is one of preferred embodiments of the present invention.

In addition, the above-mentioned β-chain polypeptide is capable of forming an HLA-A24-restricted, MAGE-A4$_{143-151}$-specific TCR together with that of an α-chain, and the phrase "β-chain polypeptide" means a polypeptide comprising a β-chain variable region polypeptide selected from a polypeptide of the amino acid sequence shown in SEQ ID NO: 7 of Sequence Listing, and a polypeptide having deletion, addition, insertion or substitution of at least one amino acid residue in the amino acid sequence shown in SEQ ID NO: 7 of Sequence Listing. The polypeptide derived from a β-chain of the TCR in the present invention contains as an essential constituent the above-mentioned amino acid sequence of a β-chain variable region, or a sequence similar thereto. A polypeptide consisting of the amino acid sequence of the entire β-chain (SEQ ID NO: 2) or a sequence similar thereto, i.e. an amino acid sequence having deletion, addition, insertion or substitution of one to several amino acid residues, the sequence containing a constant region, is one of preferred embodiments of the present invention.

The phrase "HLA-A24-restricted, MAGE-A4$_{143-151}$-specific TCR" as used herein refers to a receptor capable of specifically recognizing a complex of a peptide comprising the amino acid sequence as shown in SEQ ID NO: 9 of Sequence Listing (MAGE-A4$_{143-151}$, hereinafter simply referred to as P143) and an HLA-A24 molecule, and giving a T cell HLA-A24-restricted P143-specific cytotoxic activity against the target cell when the TCR exists on the surface of the T cell. A specific recognition of the above complex may be confirmed by a known method, and preferred methods include, for example, tetramer analysis using HLA-A24 molecule and P143, and ELISPOT assay. By performing the ELISPOT assay, it can be confirmed that a T cell expressing the TCR on the cell surface recognizes a target cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA-A24-positive target cell, such as chromium release assay.

The polypeptide of the present invention can be produced in a genetic engineering manner using the nucleic acid of the present invention described later. The HLA-A24-restricted, MAGE-A4$_{143-151}$-specific TCR is allowed to express in a cell by, for example, transducing both of the nucleic acid encoding an α-chain polypeptide and the nucleic acid encoding a β-chain polypeptide mentioned above into the cell, and allowing to express α-chain and β-chain polypeptides.

A second embodiment of the present invention relates to an HLA-A24-restricted, MAGE-A4$_{143-151}$-specific TCR, characterized in that the TCR comprises the polypeptide of the present invention. The above-mentioned TCR can be prepared in the form which is separated from naturally concomitant biological components by, for example, artificially expressing a polypeptide encoded by the nucleic acid of the present invention described later using the above-mentioned nucleic acid, without intending to particularly limit the present invention thereto.

A third embodiment of the present invention relates to a nucleic acid encoding an HLA-A24-restricted, MAGE-A4$_{143-151}$-specific TCR or a variable region thereof.

The nucleic acid of the present invention refers to a nucleic acid encoding a polypeptide comprising a TCR α-chain variable region polypeptide or a nucleic acid encoding a polypeptide comprising a TCR β-chain variable region polypeptide, in which in a case where each of the nucleic acids is transduced into a cell together with a nucleic acid encoding a TCR β-chain polypeptide or a nucleic acid encoding a TCR α-chain polypeptide, a molecule binding specifically to an HLA-A24-restricted MAGE-A4$_{143-151}$ complex is allowed to express in the above-mentioned cell. Here, the nucleic acid encoding a polypeptide comprising a TCR α-chain variable region polypeptide includes a nucleic acid encoding a TCR α-chain polypeptide and a nucleic acid encoding a TCR α-chain variable region polypeptide; and the nucleic acid encoding a polypeptide comprising a TCR β-chain variable region polypeptide includes a nucleic acid encoding a TCR β-chain polypeptide and a nucleic acid encoding a TCR β-chain variable region polypeptide. The HLA-A24-restricted, MAGE-A4$_{143-151}$-specific TCR is allowed to express in the above-mentioned cell even in cases where any of the combinations of a nucleic acid encoding a TCR α-chain polypeptide and a nucleic acid encoding a TCR β-chain polypeptide, or a nucleic acid encoding a TCR α-chain variable region polypeptide and a nucleic acid encoding a TCR β-chain variable region polypeptide are transduced into the cell.

Although not intended to limit the present invention thereto, the above-mentioned nucleic acid encoding the α-chain polypeptide is exemplified by a nucleic acid consisting of the nucleotide sequence shown in SEQ ID NO: 3 of Sequence Listing, and a nucleic acid capable of hybridizing to a nucleic acid of the above-mentioned nucleotide sequence or a complementary strand thereto under stringent conditions. The nucleic acid encoding a variable region of the α-chain polypeptide is exemplified by a nucleic acid consisting of the nucleotide sequence shown in SEQ ID NO: 6 of Sequence Listing, and a nucleic acid capable of hybridizing to a nucleic acid of the above-mentioned nucleotide sequence or a complementary strand thereto under stringent conditions. In addition, the above-mentioned nucleic acid encoding the β-chain polypeptide is exemplified by a nucleic acid consisting of the nucleotide sequence shown in SEQ ID NO: 4 of Sequence Listing, and a nucleic acid capable of hybridizing to a nucleic acid of the above-mentioned nucleotide sequence or a complementary strand thereto under stringent conditions. The nucleic acid encoding a variable region of the β-chain polypeptide is exemplified by a nucleic acid consisting of the nucleotide sequence shown in SEQ ID NO: 8 of Sequence Listing, and a nucleic acid capable of hybridizing to a nucleic acid of the above-mentioned nucleotide sequence or a complementary strand thereto under stringent conditions.

The term "stringent conditions" as referred to herein includes, for example, those conditions described, for example, in *Molecular Cloning: A Laboratory Manual, 2nd Ed.* edited by J. Sambrook et al., published by Cold Spring Harbor Laboratory, and the like. Concretely, the conditions include, for example, conditions of incubating in a solution of 6×SSC containing 0.5% SDS, 5× Denhardt's solution and 0.01% denatured salmon sperm DNA at 65° C. for 12 to 20 hours together with a probe. The nucleic acid hybridized to the probe can be detected after washing in a solution of 0.1×SSC containing 0.5% SDS at 37° C. to remove a probe non-specifically bound thereto.

The term "nucleic acid" as used herein means a single-stranded or double-stranded DNA or RNA, a DNA-RNA chimeric mixture, or a DNA-RNA hetero-double-strand. In a case where all or a part of the nucleic acids are RNA, in the sequence of the RNA moiety, "T" can be read as "U" in Sequence Listing described in the specification of the present invention. The preferred embodiment of the present invention is exemplified by combinations of two kinds of nucleic acids: a nucleic acid encoding a TCR α-chain polypeptide or a nucleic acid encoding a TCR α-chain variable region polypeptide, and a nucleic acid encoding a TCR β-chain polypeptide or a nucleic acid encoding a TCR β-chain variable region polypeptide, each in the present invention. The above-mentioned combinations of the nucleic acids are useful for the purpose of expressing the HLA-A24-restricted, MAGE-A4$_{143-151}$-specific TCR in a cell.

The nucleic acid of the present invention can be obtained, for example, as follows. RNA is prepared from an HLA-A24-restricted, MAGE-A4$_{143-151}$-specific CTL, for example, Clone #2-28 described in Non-Patent Publication 10 by a conventional method, and a cDNA is synthesized. 5'-Rapid Amplification of cDNA End (RACE) is performed with the cDNA as a template, using antisense primers complementary to a nucleic acid encoding a constant region of TCR α-chain and β-chain. The 5'-RACE may be performed by a known method, and can be performed by, for example, using a commercially available kit such as CapFishing Full-length cDNA Premix Kit (manufactured by Seegene Inc.). A DNA amplified by the above-mentioned technique is incorporated into a plasmid vector to transform *Escherichia coli*. A plasmid is produced from a transformant, and a nucleotide sequence of an inserted DNA is determined.

DNAs irrelevant to the TCR gene, amplified by the 5'-RACE can be excluded by comparing the obtained nucleotide sequence to known gene sequences of TCR α-chain and β-chain. In addition, there is a possibility that a DNA in which a mutation takes place in the nucleotide sequence during PCR is amplified; therefore, in the present invention, it is preferable that a sequence is determined from plural *Escherichia coli* clones, and that sequences of TCR α-chain gene and β-chain gene originally owned by the above-mentioned CTL, that can be deduced from the consensus sequence are used.

The nucleic acid encoding a TCR α-chain of the amino acid sequence shown in SEQ ID NO: 1 of Sequence Listing, which has the nucleotide sequence shown in SEQ ID NO: 3, and the nucleic acid encoding a TCR β-chain of the amino acid sequence shown in SEQ ID NO: 2 of Sequence Listing, which has the nucleotide sequence shown in SEQ ID NO: 4 are obtained by the above-mentioned method.

In the present invention, a DNA obtained by the method mentioned above may be used, or a nucleic acid having the same sequence may be chemically synthesized and used.

Among the nucleic acids of the present invention, the nucleic acid encoding a moiety corresponding to a variable region of each chain constituting the TCR can be connected to a region encoding a constant region or intracellular region of a nucleic acid encoding other functional molecules, for example, an antibody or a receptor. A novel nucleic acid thus constructed is useful in the production of a chimeric functional molecule to be provided with an HLA-A24-restricted, MAGE-A4$_{143-151}$-specific binding activity.

A fourth embodiment of the present invention is a recombinant nucleic acid containing the nucleic acid of the present invention. The above-mentioned recombinant nucleic acid is exemplified by a nucleic acid to which various elements that enable translation of a polypeptide encoded by the above-mentioned nucleic acid are added, in a case where the nucleic acid of the present invention is transduced into the cell, without intending to particularly limit the present invention thereto.

The recombinant nucleic acid of the present invention consisting of a DNA is exemplified by promoters (for example, promoters derived from mammals, such as phosphoglycerate kinase promoter, Xist promoter, β-actin promoter, and RNA polymerase II promoter; and promoters derived from viruses such as SV40 early promoter, cytomegalovirus promoter, thymidine kinase promoter of simple herpes virus, and LTR promoters of various retroviruses), terminators, enhancers, and those having other transcriptional controlling regions. Further, the recombinant nucleic acid may encode a sequence contributing to the translation of the polypeptide of a first invention (Kozak sequence, and the like). It is as a matter of course that each of the above elements are arranged to a functionally cooperative position, so as to be suitable in the transcription of RNA and the translation of the polypeptide from the nucleic acid of the present invention. Here, in a case where the recombinant nucleic acid is RNA, an element relating to the transcriptional control is unnecessary.

The recombinant nucleic acid of the present invention can be used by incorporating the recombinant nucleic acid into a vector as described later, or in the alternative, the recombinant nucleic acid can be used in expression of the TCR by transducing the nucleic acid of the present invention which is an RNA directly into the cell. As the method for transducing an RNA, a known method may be used, and for example, an electroporation method can be suitably used.

A fifth embodiment of the present invention relates to a vector containing at least one of the recombinant nucleic acids of the present invention, wherein the recombinant nucleic acid is inserted into the vector. The above-mentioned vector is useful in expressing an HLA-A24-restricted, MAGE-A4$_{143-151}$-specific TCR in a desired cell. Particularly preferred embodiments are exemplified by:

(1) a vector containing a recombinant nucleic acid containing a nucleic acid encoding a polypeptide comprising the TCR α-chain polypeptide of the present invention or a variable region polypeptide thereof, and a recombinant nucleic acid containing a nucleic acid encoding a polypeptide comprising the TCR β-chain polypeptide of the present invention or a variable region polypeptide thereof, wherein both of the recombinant nucleic acids are inserted into the vector; and (2) a combination of a vector containing a recombinant nucleic acid containing a nucleic acid encoding a polypeptide comprising the TCR α-chain polypeptide of the present invention or a variable region polypeptide thereof, wherein the recombinant nucleic acid is inserted into the vector, and a vector comprising a recombinant nucleic acid containing a nucleic acid encoding a polypeptide comprising the TCR β-chain polypeptide of the present invention or a variable region polypeptide thereof, wherein the recombinant nucleic acid is inserted into the vector. In the above-mentioned (1) embodiment, the nucleic acid encoding the TCR α-chain polypeptide and the nucleic acid encoding the TCR β-chain polypeptide may be each transcribed and translated under different promoters, or they may be transcribed and translated under a single promoter by using an internal ribosome entry site (IRES).

The vector used in the present invention is not particularly limited, and a proper vector may be selected and used from a known vector such as a plasmid vector or a viral vector depending upon its purpose. For example, in a case where the above-mentioned recombinant nucleic acid is incorporated into a plasmid vector, in the transduction of the incorporated plasmid vector into a cell, a method of transduction, such as calcium phosphate method, cationic lipid method, liposome method or electroporation method can be used.

A viral vector having an ability of infecting a cell and transducing a foreign DNA is suitable in the present invention. In the present invention, a known viral vector, such as a retroviral vector (including lentivirus vector and pseudo type vectors), an adenovirus vector, an adeno-associated viral vector, a herpes viral vector, can be used. The viral vector into which the recombinant nucleic acid of the present invention is inserted can be infected in an intended cell under conditions appropriate for each virus, and can transduce the nucleic acid of the present invention thereinto. The retroviral vector capable of incorporating an inserted foreign nucleic acid on chromosome is suitable in the present invention.

A sixth embodiment of the present invention relates to a cell which expresses an HLA-A24-restricted, MAGE-A4$_{143-151}$-specific TCR, characterized in that the nucleic acid of the present invention is transduced into the cell. Here, the nucleic acid of the present invention may be transduced into a desired cell as the recombinant nucleic acid of the present invention or the vector of the present invention as mentioned above. A preferred embodiment of the cell of the present invention is exemplified by a cell into which both of a nucleic acid encoding a polypeptide comprising a TCR α-chain polypeptide or a variable region polypeptide thereof, and a nucleic acid encoding a polypeptide comprising a TCR β-chain polypeptide or a variable region polypeptide thereof are transduced, and a cell transformed with the vector of the present invention. Further, the present invention also encompasses a cell in which the above-mentioned nucleic acid is incorporated on chromosomal DNA.

Since TCR plays an important role in recognizing an antigen by a T cell, a preferred embodiment of the present invention is a T cell into which the nucleic acid of the present invention is transduced. A T cell expressing an HLA-A24-restricted, MAGE-A4$_{143-151}$-specific TCR can be obtained by transducing the nucleic acid of the present invention into a T cell collected from a living body by the above-mentioned means. Further, as a preferred embodiment of the present invention, the above-mentioned nucleic acid is transduced into a cell capable of differentiating into a T cell, and thereafter the cell may be differentiated into a T cell. The cell capable of differentiating into a T cell is exemplified by, for example, hematopoietic stem cell, common lymphoid progenitor, and a precursor cell of a T cell. Here, it is not necessary that the cell to be transduced in which the nucleic acid is transduced is fractionated into a single cell species, and cell population containing the above-mentioned cell to be transduced can be a subject for the nucleic acid transduction.

The above-mentioned cell population containing the cell to be transduced may be collected from, for example, peripheral blood, bone marrow and cord blood of human or non-human mammal. If necessary, a T cell and/or a cell capable of differentiating into a T cell can be fractionated or enriched, and used in the present invention. In a case where the TCR gene-transduced cell of the present invention is used in the treatment of cancer or the like, it is preferable that the cell population is collected from the patient to be treated him/herself, or a donor having the same HLA type as the patient.

The method of transducing the nucleic acid of the present invention into a cell is not particularly limited, and a known method can be used. In a case where the nucleic acid of the present invention or the recombinant nucleic acid of the present invention is transduced, a method of using, for example, electroporation method, calcium phosphate method, cationic lipid method, or liposome method can be used. The nucleic acid can be conveniently and highly efficiently transduced by using a commercially available transfection reagent [for example, TransIT Series (manufactured by Mirus Bio Corporation), GeneJuice (manufactured by Novagene), RiboJuice (manufactured by Novagene), Lipofectamine (manufactured by Invitrogene)]. In a case where the vector of the present invention is used, the vector can be transduced into a cell in the same manner as in the above-mentioned nucleic acid as long as the vector is a plasmid vector. On the other hand, if the vector is a viral vector, an infection method suitable for each of the vectors may be selected. Especially, in a case where a retroviral vector is used, a highly efficient gene transfer can be performed against various cells, especially hematopoietic stem cell having a low infection efficiency of the retroviral vector, by using a recombinant fibronectin fragment CH-296 (manufactured by TAKARA BIO, INC.).

A seventh embodiment of the present invention relates to a carcinostatic agent, characterized in that the carcinostatic agent contains the vector of the fifth embodiment of the present invention or the cell of the sixth embodiment as an active ingredient. A T cell into which the nucleic acid of the present invention is transduced, obtained by the sixth embodiment of the present invention shows cytotoxic activity against a cell presenting an HLA-A24 molecule and MAGE-A4$_{143-151}$ peptide. Therefore, the vector and the cell of the present invention mentioned above can be used as a carcinostatic agent against a cancer expressing MAGE-A4.

The above-mentioned carcinostatic agent of the present invention is characterized in that the carcinostatic agent contains the vector or cell of the present invention as an active ingredient. The carcinostatic agent is provided in the form in which the above-mentioned vector or cell is suspended in a pharmaceutically acceptable diluent. Here, the diluent as referred to herein is, for example, a medium suitable in the storage of the vector or cell, physiological saline, or phosphate buffered saline. The medium is not particularly limited, and generally includes media such as RPMI, AIM-V, and X-VIVO10. In addition, the carcinostatic agent may be added with a pharmaceutically acceptable carrier, a preservative, or the like, for the purpose of stabilization. The carrier as referred to herein is human serum albumin, and the like. The carcinostatic agent containing the cell of the present invention as an active ingredient contains the above-mentioned cell in a density of preferably from $1 \times 10^4$ to $1 \times 10^8$ cells/mL, and more preferably from $5 \times 10^5$ to $5 \times 10^7$ cells/mL.

In a case where the carcinostatic agent containing the cell of the present invention as an active ingredient is administered to human, for example, the carcinostatic agent may be administered with an injection syringe, and the dose per adult individual is usually so that the number of cells mentioned above is preferably from $1 \times 10^6$ to $1 \times 10^{10}$ cells. Here, the above-mentioned value is a measure, and is not intended to be limited thereto. In addition, in a case of a carcinostatic agent containing the vector of the present invention as an active ingredient, the vector concentration and the dose in the carcinostatic agent greatly differ depending upon the administration route, the kinds of vectors, or the like.

As mentioned above, according to the present invention, a method of treating a cancer is provided. The above-mentioned method of treatment is an in vivo gene therapy in a case where the vector of the fifth embodiment of the present invention is used as an active ingredient. On the other hand, in a case where the cell of the present invention is used as an active ingredient, the method is an ex vivo therapy, including the step of transducing a nucleic acid encoding an HLA-A24-restricted, MAGE-A4$_{143-151}$-specific TCR into a cell isolated extracorporeally, and thereafter administering the transduced cell to a patient. The method of treatment of the present invention can use a cell derived from an individual (for example, human) to be administered, or a cell derived from an individual of which HLA type is identical into which a nucleic acid is transduced, so that toxicity is not particularly found.

EXAMPLES

The present invention will be more concretely described hereinbelow by means of Examples, without intending to limit the present invention thereto in any way.

Example 1

Cloning and Sequencing of TCR α Chain and β Chain Genes of MAGE-A4-Specific CTL Clones #2-28

(1) Preparation of RNA from #2-28, 5'-RACE, and Cloning

2-28 Cells, CTL clones showing cytotoxic activity to target cells pulsed with MAGE-A4$_{143-151}$ peptide (SEQ ID NO: 9 of Sequence Listing, hereinafter simply referred to as P143) in an HLA-A2402-restricted manner, described in Non-Patent Publication 10, were cultured, and RNA was extracted from $2 \times 10^5$ cells using RNeasy Mini Kit (manufactured by QIAGEN). cDNAs were synthesized with 200 ng of the extracted RNA as a template, using CapFishing Full-length cDNA Premix Kit (manufactured by Seegene, Inc.), in accordance with the instruction manual for the kit. Here, reverse transcription reaction was carried out using oligo dT adaptors as shown in SEQ ID NO: 10 of Sequence Listing, Reverse Transcriptase M-MLV (RNaseH free) (manufactured by TAKARA BIO INC.), and a buffer for the reaction appended to the above-mentioned enzyme.

PCR was carried out using the above-mentioned kit, with single-chain cDNAs thus obtained as a template. There were used 5'-RACE primers appended to the kit (SEQ ID NO: 11) as 5' side primers and 3-TRα-C primers specific to TCR α chain C region (SEQ ID NO: 12), 3-TRβ-C1 primers specific to TCR β chain C1 region (SEQ ID NO: 13) or 3-TRβ-C2 primers specific to TCR β chain C2 region (SEQ ID NO: 14) as 3' side primers. These reaction mixtures are referred to as PCR-α, PCR-β1 and PCR-β2, in that order. Each of the reaction mixtures was kept at 94° C. for 3 minutes, then repeated 30 cycles of reaction, wherein one cycle was 94° C. for 40 seconds, 58° C. for 40 seconds and 72° C. for 1 minute, and kept at 72° C. for 5 minutes. A part of each of the reaction products was analyzed by agarose gel electrophoresis. As a result, a DNA of about 1 kb each was amplified in PCR-α and PCR-β2.

The remaining reaction products of PCR-α and PCR-β2 were separated by agarose gel electrophoresis, and a DNA of about 1 kb each was collected from the gel. The collected products were ligated with pT7blue T-Vector (manufactured by Novagen), and *Escherichia coli* DH5α was transformed therewith.

(2) Sequencing, Clustering, and Selection of Clones

Ninety-six transformants each were selected from the transformants from PCR-α and PCR-β2 thus obtained, and plasmids were each prepared therefrom. The DNA was sequenced using an automated sequencer. A sequence of pT7blue was removed from the sequencing data, and thereafter subjected to clustering. As a result, the sequences of the longest open reading frames contained in the consensus sequences of the largest contigs were as shown in SEQ ID NO: 3 and SEQ ID NO: 4 of Sequence Listing. These sequences are cDNA sequences of TCR α chain gene and β chain gene of #2-28 cells, in turn. The amino acid sequences of TCR α chain and β chain presumed from the cDNA nucleotide sequences are shown in SEQ ID NO: 1 and SEQ ID NO: 2 of Sequence Listing. From the above-mentioned plasmids were selected plasmids having the consensus sequences of cDNA sequences of TCR α chain gene and β chain gene in the same direction as a T7 promoter of pT7blue, and the plasmids were named pBS MAGE TCRα and pBS MAGE TCRβ, respectively.

Example 2

Expression of MAGE-A4-Specific TCR According to mRNA Transfection (1) Preparation of mRNA pBS MAGE TCRα and pBS MAGE TCRβ were linearized by digestion with EcoRI restriction enzyme. In vitro transcription was carried out using mMESSAGE mMACHINE T7 Kit (manufactured by Ambion, Inc.) with the resulting products as templates, in accordance with the instruction manual for the kit. Thereafter, a poly(A) chain was added to the above-mentioned transcribed RNAs using Poly(A) Tailing Kit (manufactured by Ambion, Inc.) in accordance with the instruction manual for the kit. MAGE-A4 TCRα mRNA and MAGE-A4 TCRβ mRNA were thus obtained. The resulting products were dissolved in a phosphate buffered saline (PBS), and stored at −80° C. until use.

(2) mRNA Transfection ms69 Cells were CTL clones showing cytotoxic activity to target cells pulsed with SAGE715-723 peptide (SEQ ID NO: 15 of Sequence Listing, hereinafter simply referred to as P715), in an HLA-A2402-restricted manner, but different clones from #22 obtained in the same manner as #22 cells described in Non-Patent Publication 10. $1 \times 10^7$ ms69 cells were washed twice with X-VIVO20 medium (manufactured by Cambrex Corporation). Eighty micrograms each of MAGE-A4 TCRα mRNA and MAGE-A4 TCRβ mRNA prepared in item (1) of Example 2 were mixed with the above-mentioned cells in X-VIVO20 medium, so as to make up a total volume of 150 μL, and a transduction of the RNA into the cells was carried out according to electroporation using ECM830 Electroporation System (manufactured by BTX). The cells into which mRNA was transduced were cultured in X-VIVO20 medium at 37° C. in the presence of 5% $CO_2$ for one day. Hereinafter, the cells thus obtained are referred to as RNA-transduced ms69 cells.

Peripheral blood mononuclear cells (PBMCs) were separated from human peripheral blood according to Ficoll centrifuge method, and then washed twice with a 0.5% AB-type serum-added PBS. MACS CD8 MicroBeads (manufactured by Miltenyi Biotec KK), magnetic beads to which an anti-CD8 antibody was immobilized, were added thereto, and the mixture was reacted at 4° C. for 15 minutes. Thereafter, the beads were washed once with a 0.5% AB-type serum-added PBS. CD8 positive cells that were collected from magnetic beads trapped by a column equipped with a magnet were suspended in RPMI 1640 medium to which a 10% AB-type serum and 100 U/mL interleukin 2 (IL-2) were added, so as to have a density of $1\times10^6$ cells/mL. An anti-CD3 antibody (Orthoclone OKT3, manufactured by JANSSEN PHARMACEUTICAL K.K.) diluted with PBS so as to have a concentration of 1 μg/mL was added to each well of a 24-well plate in a volume of 300 μL/well each. The mixture was allowed to stand at 4° C. overnight, the supernatant was then discarded, and the suspension of CD8 positive cells mentioned above was put in each well in a volume of 1 mL/well each. The cells were cultured at 37° C. in the presence of 5% $CO_2$ while a half the volume of the medium was replaced on the fourth day, the seventh day and the tenth day from the initiation of culture. $1\times10^7$ CD8 positive cells on the twelfth day from the initiation of culture were washed twice with X-VIVO20 medium (manufactured by Cambrex Corporation). MAGE-A4 TCRα mRNA and MAGE-A4 TCRβ mRNA were transduced into the above-mentioned cells in the same manner as in the ms69 cells. The cells into which mRNA was transduced were cultured in X-VIVO20 medium at 37° C. in the presence of 5% $CO_2$ for one day. The cells thus obtained are hereinafter referred to as RNA-transduced CD8 positive cells.

(3) Tetramer Assay

A polypeptide, which is HLA-A2402 heavy chain having addition of a sequence acting as a substrate of biotin protein ligase BirA at a C-terminal, and β2-microglobulin were allowed to express in *Escherichia coli* as an insoluble inclusion body. The above-mentioned inclusion body was refolded in vitro, in the presence of P143 peptide, and whereby an HLA-A2402/β2-microglobulin/P143 complex was formed. Biotin protein ligase (manufactured by Avidity Inc.) was allowed to act on the resulting complex, and a tetramer was prepared using a phycoerythrin-labeled streptavidin (Streptavidin-PE, manufactured by Invitrogen).

The above-mentioned RNA-transduced ms69 cells and RNA-transduced CD8 positive cells were reacted with 20 μg/mL tetramer at 37° C. for 30 minutes, and thereafter reacted with a Tricolor-labeled mouse anti-human CD8 antibody (manufactured by CALTAG) on ice for 15 minutes. The cells were washed, and thereafter flow cytometry analysis was carried out using FACS Calibur (manufactured by Becton, Dickinson and Company). The ms 69 cells and the CD8 positive cells were used as negative controls, and the #2-28 cells as a positive control.

Figure 2:
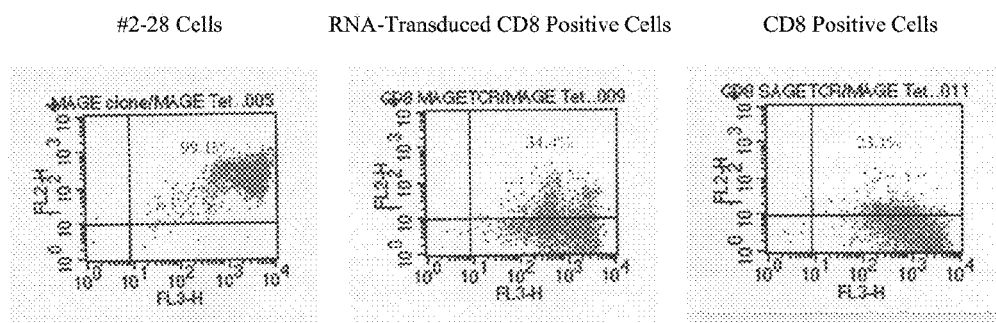
[FIG. 2] Graphs showing the results of tetramer assay of #2-28 cells, RNA-transduced CD8 positive cells, and CD8 positive cells.

As a result, a positive percentage of the tetramer was 66.5% in the RNA-transduced ms69 cells, in contrast to 0.60% in the ms69 cells which were a negative control, and a positive percentage of the tetramer was 34.4% in the RNA-transduced CD8 positive cells, in contrast to 23.1% in the CD8 positive cells which were a negative control. The results of tetramer assay of the ms69 cells and CD8 positive cells into which RNA was transduced are shown in FIG. 1 and FIG. 2. It was clarified from the results that gene products of TCR α chain and TCR β chain cloned from the #2-28 cells could recognize a complex of P143 and HLA-A2402.

(4) ELISPOT Assay

Target cells were prepared as follows. T2-A24 cells prepared by transfecting HLA-2402 gene into B×T hybrid cell line 174CEM. T2 (hereinafter simply referred to as T2 cells) (Ikuta Y. et al. *Blood*, 99, 3717-3724 (2002)) were cultured in RPMI 1640 medium containing 10% fetal calf serum (FCS), the cultured medium was centrifuged, and the supernatant was then discarded. Thereafter, the cells were washed by suspending the resulting residue in RPMI 1640 medium, centrifuging the suspension, and then discarding the supernatant. The procedures of washing the cells in the manner as described above were carried out 3 times in total, and thereafter the washed cells were suspended in RPMI 1640 medium containing 1 mL of 10 μM P143 or P715 or without containing peptide, and the suspension was incubated at 37° C. in the presence of 5% $CO_2$ for 1 hour. The cells were collected by centrifugation, and the cells were then washed by suspending the collected cells in RPMI 1640 medium, and centrifuging the suspension. The cells were suspended in RPMI 1640 medium so as to have a density of $5\times10^4$ cells/100 μL, and the suspension was used as the target cells of ELISPOT assay.

An anti-human interferon γ antibody (1-D1K, manufactured by Mabtech AB) diluted with PBS so as to have a concentration of 2 μg/mL was put in each well of MultiScreen HA 96-well filter and assay plate (manufactured by Millipore Corporation) in a volume of 100 μL/well each, and allowed to stand at 4° C. overnight. The liquid in the wells was discarded, and thereafter the plate was washed by adding RPMI 1640 medium to each well in a volume of 100 μL/well each, allowing the mixture to stand for 15 minutes, and discarding the liquid. The washing procedures were carried out one more time, and thereafter RPMI 1640 medium containing 10% AB-type serum was added to each well, and the mixture was allowed to stand at 37° C. for 1 hour to carry out blocking. After the blocking, the supernatant was aspirated, and thereafter the plate was washed by adding RPMI 1640 medium to each well in a volume of 100 μL each. The washing procedures were carried out 3 times in total.

(a) The RNA-transduced ms69 cells, (b) the ms69 cells which were a negative control and (c) the #2-28 cells which were a positive control, each prepared in item (2) of Example 2, and (d) the RNA-transduced CD8 positive cells and (e) the CD8 positive cells which were a negative control, each prepared in item (2) of Example 2 were collected by centrifugation, and the collected cells were once washed with RPMI 1640 medium. The cells (a), (b) and (c) were suspended in RPMI 1640 medium, so as to have a density of 2000 cells/100 μL, 1000 cells/100 μL or 500 cells/100 μL, and the cells (d) and (e) were suspended so as to have a density of $2\times10^4$ cells/100 μL, and the suspension was put in the wells of washed plate prepared in item (4) of Example 2 in a volume of 100 μL/well each. The suspension of target cells mentioned above was added thereto in a volume of 100 μL each, and the mixture was cultured at 37° C. in the presence of 5% $CO_2$ for 20 hours.

The liquid was removed from each well of the plate and each well was washed 6 times with PBS containing 0.05% Tween 20 (PBS-T). Biotinylated anti-human interferon γ antibodies (manufactured by Mabtech AB, a clone name of 7-B6-1) were diluted with PBS so as to have a concentration of 0.2

μg/mL, and the dilution was put in each well in a volume of 100 μL each, and thereafter allowed to stand at 4° C. overnight.

The liquid was removed from each well of the plate, and each well was washed 6 times with PBS-T. An alkaline phosphatase-labeled streptavidin (manufactured by Bio-Rad Japan) diluted with PBS so as to have a concentration of 1 μg/mL was put in each well in a volume of 100 μL each, and the mixture was reacted at room temperature for 1 hour. The liquid was removed from each well of the plate, and each well was washed 3 times with PBS-T. Thereafter, a color development solution prepared in accordance with the instruction manual for AP Color Development Kit (manufactured by Bio-Rad Japan, 170-6432) was put in each well in a volume of 100 μL each, and a color development reaction was carried out with shading. The color development was stopped with distilled water, and a photograph of the plate was taken.

Figure 3:
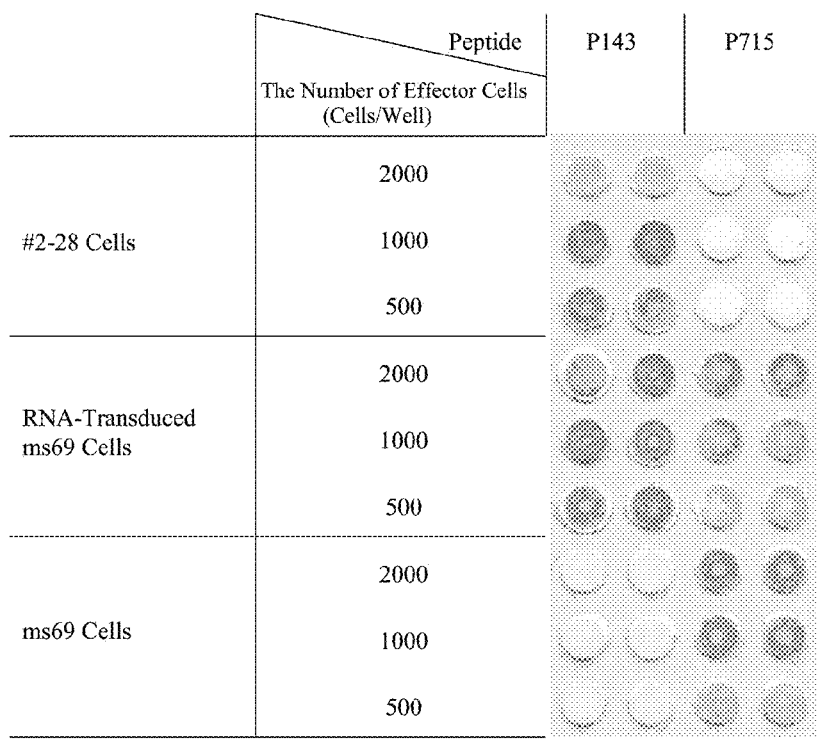
[FIG. 3] A chart showing the results of ELISPOT assay of #2-28 cells, RNA-transduced ms69 cells, and ms69 cells.
Figure 4:
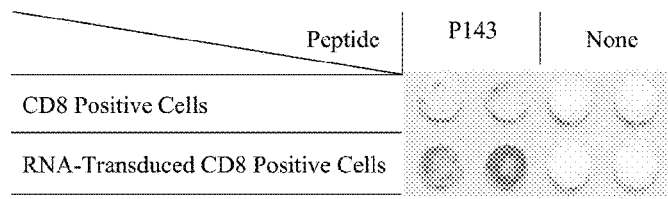
[FIG. 4] A chart showing the results of ELISPOT assay of RNA-transduced CD8 positive cells, and CD8 positive cells.

As a result, the ms69 cells and CD8 positive cells into which RNA was transduced formed a larger number of interferon γ positive spots when the target cells were pulsed with P143, as compared to those of the ms69 cells and the CD8 positive cells. The results are shown in FIG. 3 and FIG. 4. FIG. 3 is the results of ELISPOT assay when the CTL clones were used as effector cells. A large number of interferon γ positive spots were formed by the ms69 cells to the target cells pulsed with P715, the #2-28 cells to the target cells pulsed with P143, and the RNA-transduced ms69 cells to both target cells. FIG. 4 is the results of ELISPOT assay when the CD8 positive cells were used as effector cells. Interferon γ positive spots were formed by the RNA-transduced CD8 positive cells, specific to the target cells pulsed with P143.

(5) Cytotoxic Activity

The T2 cells, the T2-A24 cells, and T2-A2 cells prepared by transfecting HLA-A0201 gene into T2 cells were washed 3 times with RPMI 1640 medium, and the washed cells were suspended in RPMI 1640 medium so as to have a density of $5\times10^6$ cells/mL. P143 or P715 was added to 1 mL each of the above-mentioned cell suspensions so as to have a final concentration of 10 μM, and the mixture was allowed to stand at room temperature for 15 minutes. Thereafter, 1 mL each of RPMI 1640 medium containing 10% FCS was added thereto, and the mixture was incubated at 37° C. for 1 hour. The cells were washed 3 times with RPMI 1640 medium without containing FCS, and $1\times10^6$ cells were suspended in 100 μL of RPMI 1640 medium containing 10% FCS. Fifty microliters of an aqueous $Na_2^{51}CrO_4$ solution (3.7 MBq) was added thereto, and the mixture was labeled at 37° C. for 2 hours. The resulting cells were used as the target cells for the determination of cytotoxic activity.

The ms69 cells, the RNA-transduced ms69 cells, the #2-28 cells, the CD8 positive cells, and the RNA-transduced CD8 cells were washed twice with RPMI 1640 medium, and the washed cells were suspended in RPMI 1640 medium containing 10% FCS so as to have a density of $2\times10^6$ cells/mL, $1\times10^6$ cells/mL, $5\times10^5$ cells/mL, $2.5\times10^5$ cells/mL, $1.25\times10^5$ cells/mL, an $6.25\times10^4$ cells/mL (effector cells), respectively, and a 100 μL portion thereof was put in each well of a 96-well V-bottom plate. The target cells were suspended in RPMI 1640 medium containing 10% FCS so as to have a density of $1\times10^6$ cells/mL, and the suspension was added to each well with the effector cells in a volume of 100 μL each. The mixture was reacted at 37° C. for 4 hours, and thereafter the supernatants were collected by centrifugation, and an amount of $^{51}Cr$ released to 100 μL of the supernatant was determined by using a gamma counter. The specific cytotoxic activity was calculated from the measured value of radioactivity according to the following formula.

Specific Cytotoxic Activity (%)=[(Measured Value in Each Well−Minimum Release Value)/ (Maximum Release Value−Minimum Release Value)]×100   [Formula 1]

In the above-mentioned formula, the minimum release value is the amount of $^{51}Cr$ released in the well to which the effector cells are not added, showing the amount of $^{51}Cr$ naturally released from the target cells. In addition, the maximum release value shows the amount of $^{51}Cr$ released when the cells are disrupted by adding Triton X-100 to the target cells.

Figure 5:
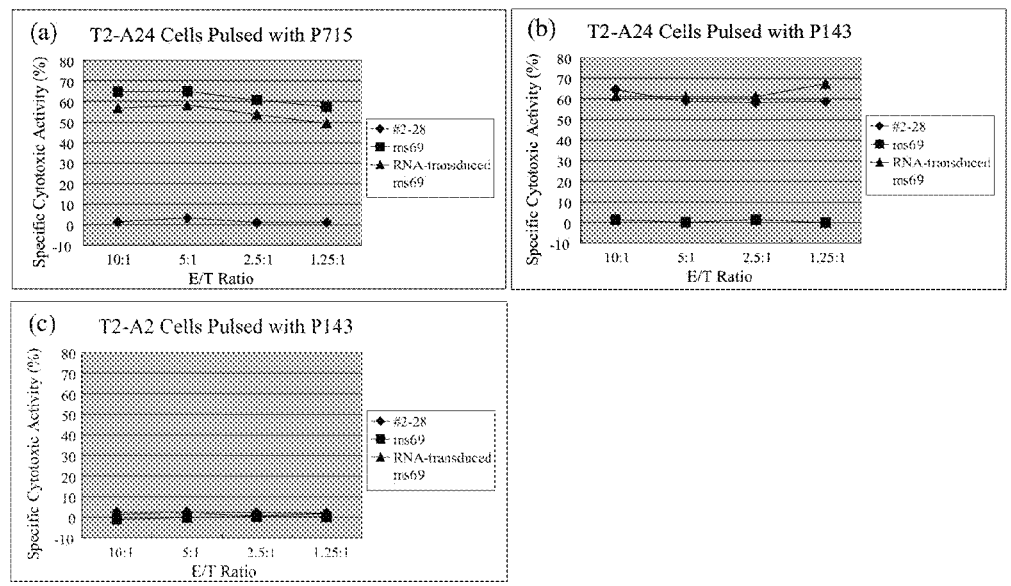
[FIG. 5] Graphs showing cytotoxic activity of #2-28 cells, RNA-transduced ms69 cells, and ms69 cells.
Figure 6:
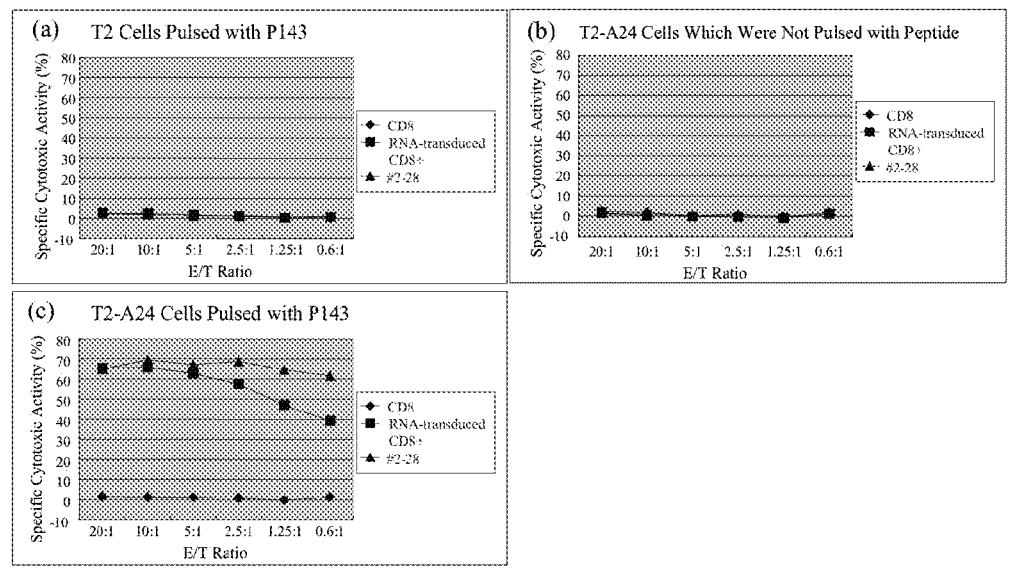
[FIG. 6] Graphs showing cytotoxic activity of #2-28 cells, RNA-transduced CD8 positive cells, and CD8 positive cells.

The results are shown in FIG. 5 and FIG. 6. FIG. 5 is graphs showing cytotoxic activity of CTL clones to (a) T2-A24 cells pulsed with P715, (b) T2-A24 cells pulsed with P143, and (c) T2-A2 cells pulsed with P143, and the axis of abscissas shows a ratio of the number of effector cells/the number of target cells (E/T ratio), and the axis of ordinates shows specific cytotoxic activity (%). The ms69 cells showed cytotoxic activity only to the T2-A24 cells pulsed with P715, and the #2-28 cells showed cytotoxic activity only to the T2-A24 cells pulsed with P143; in contrast, the ms69 cells into which RNA was transduced showed cytotoxic activity to both target cells. Any of the effector cells did not show cytotoxic activity to the T2-A2 cells pulsed with P143. FIG. 6 is graphs showing cytotoxic activity of CD8 cells to (a) T2 cells pulsed with P143, (b) T2-A24 cells which were not pulsed with peptide, and (c) T2-A24 cells pulsed with P143, and the axis of abscissas shows the E/T ratio, and the axis of ordinates shows specific cytotoxic activity (%). The CD8 positive cells into which RNA was transduced and the #2-28 cells which are a positive control showed cytotoxic activity to the T2-A24 cells pulsed with P143, while the CD8 positive cells which are a negative control did not show cytotoxic activity to any of the cells.

It was clarified from the above results that the gene encoding TCR α chain and β chain of #2-28 cells gives a P143-specific HLA-A2402-restricted cytotoxic activity to the CTL clones and the CD8 cells derived from peripheral blood.

Industrial Applicability

According to the present invention, a HLA-A24-restricted, TCR α chain and β chain polypeptide to MAGE-A4, derived from CTL, and a nucleic acid encoding the polypeptide are provided. Since the above-mentioned nucleic acid can give T cells cytotoxic activity to a cell presenting HLA-A24 molecule and MAGE-A4$_{143-151}$ peptide, the above-mentioned nucleic acid is useful in the treatment of a cancer that expresses MAGE-A4.

Sequence Listing Free Text

SEQ ID NO: 10; Oligo dT adaptor.

SEQ ID NO: 11; 5'-RACE primer.

SEQ ID NO: 12; Synthetic primer 3-TRalpha-C to amplify a DNA fragment encoding TCR alpha chain.

SEQ ID NO: 13; Synthetic primer 3-TRbeta-C1 to amplify a DNA fragment encoding TCR beta chain.

SEQ ID NO: 14; Synthetic primer 3-TRbeta-C2 to amplify a DNA fragment encoding TCR beta chain.

The invention claimed is:

1. A recombinant cell transduced with a recombinant nucleic acid encoding a polypeptide comprising the amino acid sequence of SEQ ID NO:5 wherein expression of the nucleic acid results in production of a polypeptide that, when in combination with a polypeptide set forth in either of SEQ ID NO:2 or SEQ ID NO:7, is capable of forming a receptor that specifically binds to an HLA-A24-restricted, MAGE-A4$_{143-151}$ complex.

2. A recombinant cell wherein both of a first recombinant nucleic acid encoding a first polypeptide comprising the amino acid sequence of SEQ ID NO:5 and a second recombinant nucleic acid encoding a second polypeptide comprising the amino acid sequence of SEQ ID NO:7 are transduced into the cell resulting in expression of a HLA-A24-restricted, MAGE-A4$_{143-151}$ T cell receptor.

3. A recombinant cell transformed with a vector selected from the group consisting of:
  (a) a vector comprising a recombinant nucleic acid encoding a polypeptide comprising the amino acid sequence of SEQ ID NO:5,
  (b) a vector comprising a recombinant nucleic acid encoding a polypeptide comprising the amino acid sequence of SEQ ID NO: 7,
  (c) a vector comprising a recombinant nucleic acid encoding a polypeptide comprising the amino acid sequence of SEQ ID NO:5 and a recombinant nucleic acid encoding a polypeptide comprising the amino acid sequence of SEQ ID NO:7, and
  (d) a combination of a vector comprising a recombinant nucleic acid encoding a polypeptide comprising the amino acid sequence of SEQ ID NO:5 and a recombinant nucleic acid encoding a polypeptide comprising the amino acid sequence of SEQ ID NO:7,
  wherein expression of the nucleic acid or nucleic acids result in production of a polypeptide or polypeptides that are capable of forming a receptor that specifically binds to an HLA-A24-restricted, MAGE-A4$_{143-151}$ complex.

4. A recombinant T cell or cell capable of differentiating into a T cell transduced with a recombinant nucleic acid encoding a polypeptide comprising the amino acid sequence of SEQ ID NO:5 wherein expression of the nucleic acid results in production of a polypeptide that, when in combination with a polypeptide set forth in either SEQ ID NO:2 or SEQ DI NO:7, is capable of forming a receptor that specifically binds to an HLA-A24-restricted, MAGE-A4$_{143-151}$ complex.

5. A carcinostatic agent comprising, as an active ingredient, a recombinant cell transformed with a vector selected from the group consisting of:
  (a) a vector comprising a recombinant nucleic acid encoding a polypeptide comprising the amino acid sequence of SEQ ID NO:5,
  (b) a vector comprising a recombinant nucleic acid encoding a polypeptide comprising the amino acid sequence of SEQ ID NO: 7,
  (c) a vector comprising a recombinant nucleic acid encoding a polypeptide comprising the amino acid sequence of SEQ ID NO:5 and a recombinant nucleic acid encoding a polypeptide comprising the amino acid sequence of SEQ ID NO:7, and
  (d) a combination of a vector comprising a recombinant nucleic acid encoding a polypeptide comprising the amino acid sequence of SEQ ID NO:5 and a recombinant nucleic acid encoding a polypeptide comprising the amino acid sequence of SEQ ID NO:7,
  wherein expression of the nucleic acid or nucleic acids results in production of a polypeptide or polypeptides that are capable of forming a receptor that specifically binds an HLA-A24-restricted, MAGE-A4$_{143-151}$ complex.

6. A carcinostatic agent comprising a cell transduced with a first recombinant nucleic acid encoding a first polypeptide comprising the amino acid sequence of SEQ ID NO:5 and a second recombinant nucleic acid encoding a second polypeptide sequence comprising the amino acid sequence of SEQ ID NO: 7 wherein expression of the nucleic acids result in production of polypeptides that are capable of forming a receptor that specifically binds to an HLA-A24-restricted, MAGE-A4$_{143-151}$ complex.

7. A recombinant cell transduced with a recombinant nucleic acid encoding a polypeptide comprising the amino acid sequence of SEQ ID NO:7 wherein expression of the nucleic acid results in production of a polypeptide that, when in combination with a polypeptide set forth in either SEQ ID NO:2 or SEQ ID NO:7 is capable of forming a receptor that specifically binds to an HLA-A24-restricted, MAGE-A4$_{143-151}$ complex.

8. A recombinant T cell or cell capable of differentiating into a T cell transduced with a recombinant nucleic acid encoding a polypeptide comprising the amino acid sequence of SEQ ID NO:7 wherein expression of the nucleic acid results in production of a polypeptide that, when in combination with a polypeptide set forth in either of SEQ ID NO:1 or SEQ ID NO:5, is capable of forming a receptor that specifically binds to an HLA-A24-restricted, MAGE-A4$_{143-151}$ complex.

9. The recombinant cell of claim 1, wherein recombinant nucleic acid encoding the polypeptide comprises the amino acid sequence of SEQ ID NO:1.

10. The recombinant cell of claim 1, wherein the nucleic acid encoding the polypeptide consists of the amino acid sequence of SEQ ID NO:5.

11. The recombinant cell of claim 2, wherein the first polypeptide comprises the amino acid sequence of SEQ ID NO:1 and wherein the second polypeptide comprises the amino acid sequence of SEQ ID NO:2.

12. The recombinant cell of claim 2, wherein the first polypeptide consists of the amino acid sequence of SEQ ID NO:5 and wherein the second polypeptide consists of the amino acid sequence of SEQ ID NO:7.

13. The recombinant T cell or cell capable of differentiating into a T cell of claim 4, wherein the recombinant nucleic acid encoding the polypeptide comprises SEQ ID NO:1.

14. The recombinant T cell or cell capable of differentiating into a T cell of claim 4, wherein the recombinant nucleic acid encodes the polypeptide consisting of SEQ ID NO:5.

15. The carcinostatic agent comprising the cell of claim 6, wherein the first recombinant nucleic acid encodes the polypeptide comprising the amino acid sequence of SEQ ID NO:1.

16. The carcinostatic agent comprising the cell of claim 6, wherein the first recombinant nucleic acid encodes the polypeptide consisting of the amino acid sequence of SEQ ID NO:5.

17. The recombinant cell of claim 7 wherein the recombinant nucleic acid encodes a polypeptide comprising the amino acid sequence set forth in SEQ ID NO:2.

18. The recombinant cell of claim 7 wherein the recombinant nucleic acid encodes a polypeptide consisting of the amino acid sequence set forth in SEQ ID NO:7.

19. The recombinant T cell or cell capable of differentiating into a T cell of claim 8, wherein the recombinant nucleic acid encoding the polypeptide comprises SEQ ID NO:2.

20. The recombinant T cell or cell capable of differentiating into a T cell of claim 8, wherein the recombinant nucleic acid encodes the polypeptide consisting of SEQ ID NO:7.

* * * * *